(12) United States Patent
Chalmers et al.

(10) Patent No.: US 7,502,119 B2
(45) Date of Patent: Mar. 10, 2009

(54) THIN-FILM METROLOGY USING SPECTRAL REFLECTANCE WITH AN INTERMEDIATE IN-LINE REFERENCE

(75) Inventors: Scott A. Chalmers, San Diego, CA (US); Randall S. Geels, San Diego, CA (US)

(73) Assignee: Filmetrics, Inc., San Diego, CA (US)

( * ) Notice: Subject to any disclaimer, the term of this patent is extended or adjusted under 35 U.S.C. 154(b) by 0 days.

(21) Appl. No.: 11/699,262

(22) Filed: Jan. 29, 2007

(65) Prior Publication Data
US 2008/0180684 A1 Jul. 31, 2008

(51) Int. Cl.
*G01B 9/02* (2006.01)
(52) U.S. Cl. ...................................... 356/477
(58) Field of Classification Search .................. 356/503, 356/504, 630–632, 477, 482
See application file for complete search history.

(56) References Cited

U.S. PATENT DOCUMENTS

| | | | | |
|---|---|---|---|---|
| 5,381,229 A | * | 1/1995 | Murphy et al. | 356/477 |
| 5,402,230 A | * | 3/1995 | Tian et al. | 356/482 |
| 7,304,744 B1 | * | 12/2007 | Hatanaka et al. | 356/477 |
| 2005/0018199 A1 | * | 1/2005 | LeBlanc | 356/477 |
| 2006/0109479 A1 | * | 5/2006 | Tai et al. | 356/482 |
| 2006/0126991 A1 | * | 6/2006 | Huang | 385/12 |
| 2007/0133002 A1 | * | 6/2007 | Wax et al. | 356/456 |

* cited by examiner

*Primary Examiner*—Tarifur Chowdhury
*Assistant Examiner*—Jonathan M Hansen
(74) *Attorney, Agent, or Firm*—Courtney Staniford & Gregory LLP

(57) ABSTRACT

Reflectance systems and methods are described that use information of an intermediate reference signal to continuously monitor, detect and/or compensate for drift in a metrology system. The intermediate reference signal is present regardless of whether a sample is being measured. The reflectance system comprises components including a transmission element coupled to a sample area and a receiver. The transmission element is configured to route signals between components of the system. The signals include an illumination signal, and a sample signal resulting from interaction of the illumination signal with a sample when the sample is present in the sample area. The signals also include the reference signal that results from interaction of the illumination signal with one or more components of the system.

26 Claims, 5 Drawing Sheets

THIN-FILM METROLOGY USING SPECTRAL REFLECTANCE WITH AN INTERMEDIATE IN-LINE REFERENCE

TECHNICAL FIELD

This invention relates generally to the field of thin-film metrology.

BACKGROUND

Many products use film layers to modify surface characteristics. Polycarbonate ophthalmic lenses, for example, use a film hardcoat layer to protect against scratching and chemical attack. The thicknesses of films used in different applications can range from 0.0001 micron (less than an atom thick) to several hundreds of microns. It is usually important to control the thickness of films used, whether to optimize the performance of the film, or simply to minimize the amount of film precursor that is used.

The most common method of measuring the thickness of non-opaque films less than 100 microns thick is spectral reflectance. Spectral reflectance methods first acquire a range of wavelengths of light reflected off the film structure, and then analyze this reflectance spectrum to determine the film thickness (and often other properties). See for example "Taking the Mystery Out of Thin-Film Measurement," or, "Spectroscopic Ellipsometry and Reflectometry: A User's Guide" by Tompkins and McGahan, John Wiley & Sons, 1999.Companies such as Filmetrics, Inc. of San Diego, Calif. manufacture such spectral reflectance systems.

Accurate determination of film thickness requires acquiring reflectance spectra that are an accurate representation of the film structure, i.e., the reflectance spectra must be significantly free from contributions from the measuring apparatus. The light reflected off of the film is generally measured using a spectrometer. The amount of light measured at each wavelength is a product of the light source, the film structure, the spectrometer, and the various intermediate optical components used to direct and collect the light. To determine the reflectance spectrum of the film structure, the contributions of the other system components are determined by substituting a known reflectance standard for the film structure, and using the resulting reflectance signal to normalize the subsequent film structure measurements.

Because the reference reflectance standard can not be taken simultaneously with the film structure reflectance, substantial drift in the normalization can occur over time, and this leads to degradation of the quality of the film structure reflectance spectra and, subsequently, the thickness measurement accuracy. Configurations as described above, where the reference is taken before and/or after the film reflectance measurement, are known as "single-beam" reflectance systems. In practice, references taken with single-beam configurations take operator intervention, which means that the time interval between references is generally large and that errors are possible. The result is that operator time is consumed and measurement accuracy degrades.

The primary alternative to the single-beam configuration is the dual-beam configuration, which splits off a portion of the light source and routes it to a second spectrometer. This allows for real-time monitoring of and correction for light source drift. However, dual-beam configurations are almost twice as expensive as single-beam configurations (since the spectrometer is usually the most expensive system component) and they do not take into account spectrometer drift or that of most of the optical path. An excellent review of single- versus dual-beam configurations, as well as patent literature relevant to this application, is included in U.S. Pat. No. 6,831, 740 for example. Consequently, there is a need for systems and methods that provide an intermediate in-line nearly real-time reference for single-beam reflectance configurations.

INCORPORATION BY REFERENCE

Each publication, patent, and/or patent application mentioned in this specification is herein incorporated by reference in its entirety to the same extent as if each individual publication, patent and/or patent application was specifically and individually indicated to be incorporated by reference.

BRIEF DESCRIPTION OF THE DRAWINGS

The components in the figures are not necessarily to scale, emphasis instead being placed upon illustrating the principles of the embodiments. In the figures, like reference numerals designate corresponding parts throughout the different views.

DETAILED DESCRIPTION

Reflectance systems and methods are described below that include a reflectance system comprising components including a transmission element coupled to a sample area and a receiver. The transmission element, which in an embodiment is an optical fiber, is configured to route signals between the components of the system. The signals include an illumination signal. The signals further include a sample signal resulting from interaction of the illumination signal with a sample when the sample is present in the sample area. The signals also include a reference signal that results from interaction of the illumination signal with one or more components of the system. The reference signal is present continuously, regardless of presence of the sample signal, and is used to monitor and/or compensate for drift of the components. Monitoring and/or compensating for drift as described herein includes monitoring and/or compensating for changes in one or more system components.

The reflectance systems and methods described below include a metrology method comprising coupling an illumination signal to components of a metrology system. The metrology method includes receiving a sample signal that results from interaction of the illumination signal with a sample when the sample is present and under analysis by the metrology system. The metrology method further includes receiving a reference signal that results from interaction of the illumination signal with at least one component of the metrology system components. The reference signal is present in the metrology system and received regardless of receipt of the sample signal. The method includes monitoring and/or compensating for drift of the components using the reference signal.

The reflectance system of an embodiment functions or operates to provide a reference signal that is an intermediate in-line nearly real-time reference for single-beam reflectance configurations. Accordingly, the reference signal, which is present whether or not a sample is under analysis by the host system, can be monitored at times close enough to the film sample measurements as to be practically simultaneous. This intermediate-reference reflection can then be used to detect and compensate for system drift as described in detail below.

In the following description, numerous specific details are introduced to provide a thorough understanding of, and enabling description for, embodiments of the reflectance systems. One skilled in the relevant art, however, will recognize that these embodiments can be practiced without one or more of the specific details, or with other components, systems, etc. In other instances, well-known structures or operations are not shown, or are not described in detail, to avoid obscuring aspects of the disclosed embodiments.

Figure 1:
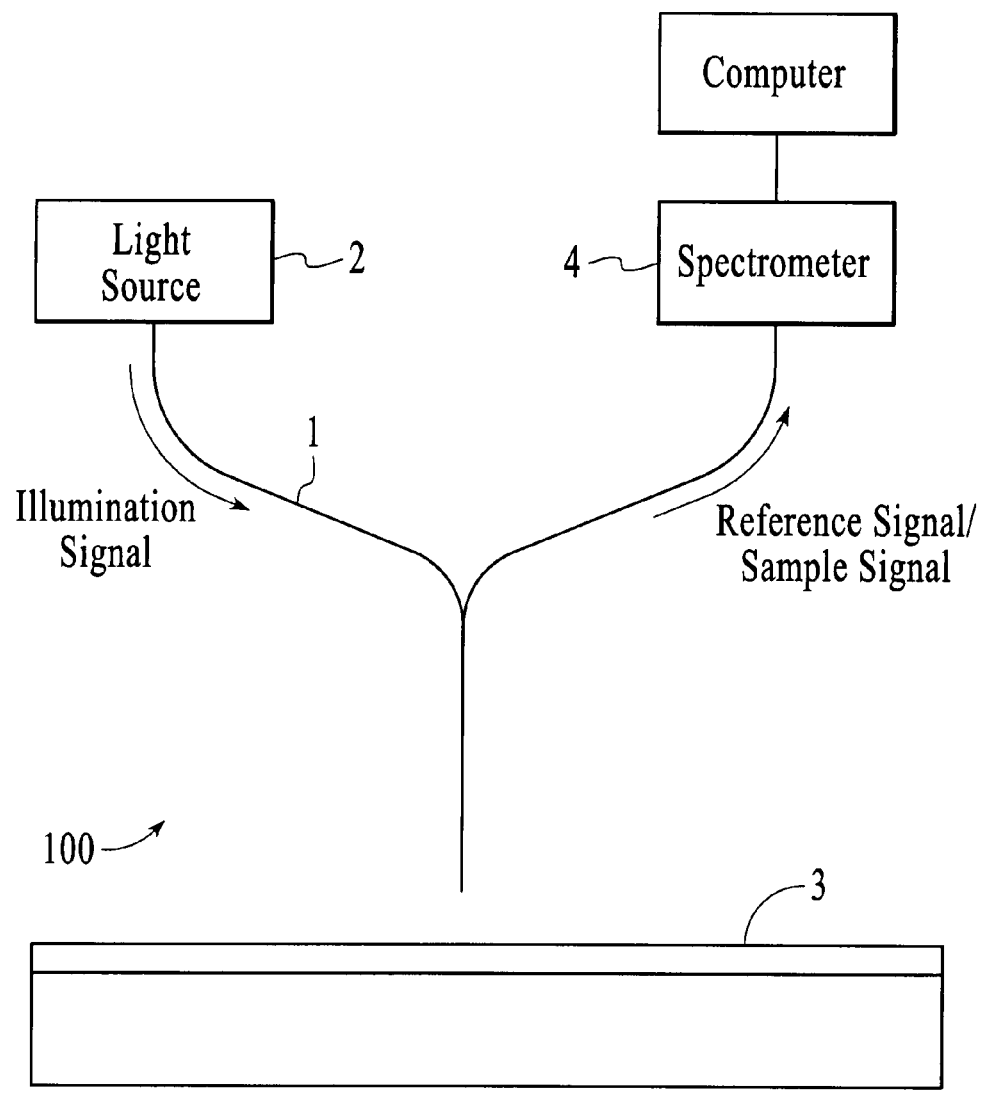
FIG. 1 is a reflectance system configured to include a reference signal, under an embodiment.

FIG. 1 is a reflectance system 100 configured to include a reference signal, under an embodiment. The reference signal as described herein is an intermediate in-line nearly real-time reference. The reflectance system is representative of, for example, the Filmetrics F20-HC system available from Filmetrics, Inc. of San Diego, Calif. The reflectance system is in the "contact probe" configuration but is not limited to this configuration. The system 100 includes a transmission element 1 in a "Y" fused splitter configuration, and the transmission element 1 is configured to deliver an illumination signal from a signal source 2 to a film structure 3 (of a sample that is present for analysis by the system). The transmission element 1 is further configured to collect and deliver signals to a receiver 4. The collected signals always include a reference signal; when the sample 3 is present and under analysis by the system 100 the collected signals include a sample signal.

As a more specific example, the "Y" fused transmission element 1 is a splitter fiber 1 configured to deliver light (illumination signal) from light source 2 (signal source) to the film structure 3 (sample), and to collect and deliver the reflected light (collected signal) to the spectrometer 4 (receiver). The splitter fiber includes an optical fiber or optical transmission element having a single fiber at the common end of the "Y", which carries both the illumination signal and reflected or return signals.

In single-beam operation the system 100 measures a sample (and also a reference) by placing it in close proximity (e.g., approximately in a range of 0.1 mm to 2 mm) to the distal end of the fiber 1. Because light is reflected from any interface that has a discontinuity in refractive index, the reflected signal (e.g., light) traveling back to the receiver of an embodiment includes components reflected from both the sample and the fiber end, for example. The reflected signal in the presence of a sample (e.g., reference sample, film sample, etc.), therefore, includes the reference signal reflected from the distal end of the fiber and the sample signal reflected from the sample.

Figure 2:
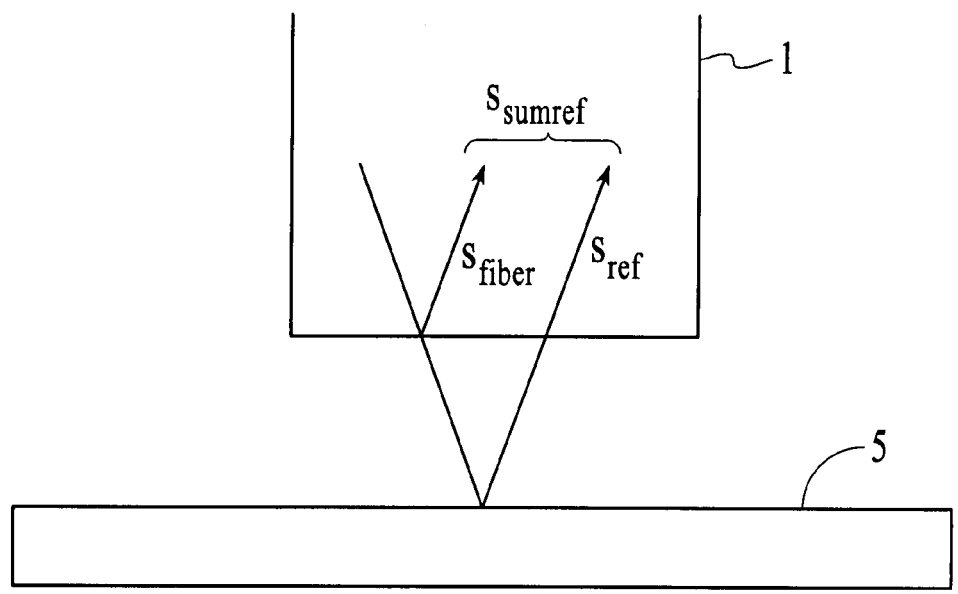
FIG. 2 shows reflectance components $S_{fiber}$ and $S_{ref}$ when a reference sample is under analysis in the reflectance system, under an embodiment.
Figure 3:
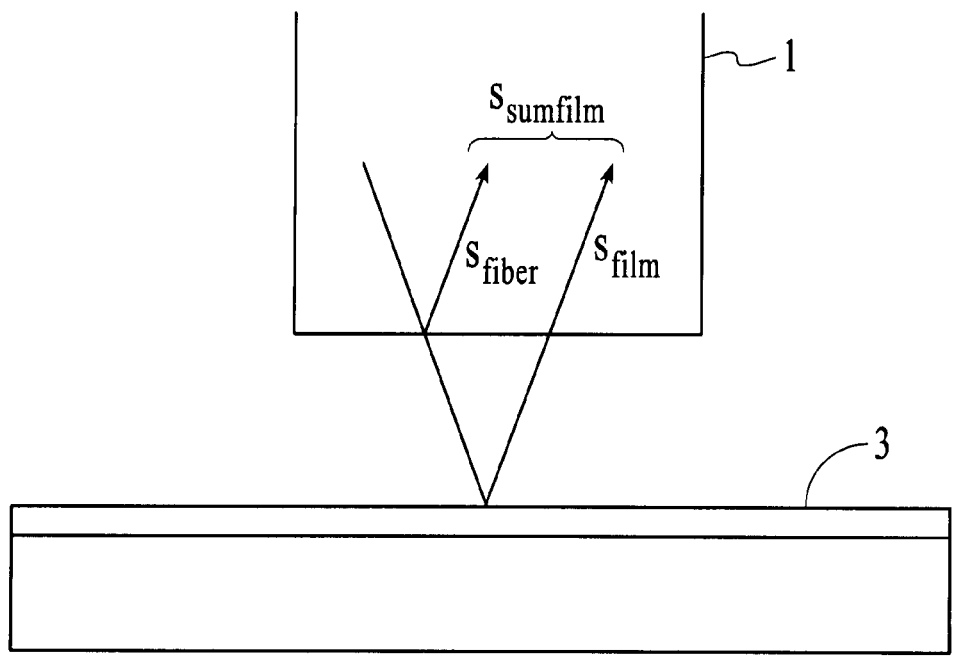
FIG. 3 shows reflectance components $S_{fiber}$ and $S_{film}$ when a film sample is under analysis in the reflectance system, under an embodiment.

FIG. 2 shows reflectance components $S_{fiber}$ and $S_{ref}$ when a reference sample 5 is under analysis in the reflectance system 100, under an embodiment. FIG. 3 shows reflectance components $S_{fiber}$ and $S_{film}$ when a film sample 3 is under analysis in the reflectance system 100, under an embodiment. The reflectance components $S_{fiber}$ (representing the fiber-end reference signal), $S_{ref}$ (representing a reference sample signal from a reference sample 5), and/or $S_{film}$ (representing a film sample signal from a film sample 3) are shown near the end of the fiber for a sample, but are not so limited. References herein to "sample" include one or more of a "reference sample" and a "film sample" but are not so limited. Ignoring detector "dark" signal levels that are measured and subtracted (by measuring pixels masked for this purpose for example), the reflectance of the film sample can be calculated at each wavelength using Equation 1 as follows:

$$R = R_{ref} * (S_{film}/S_{ref}) = R_{ref} * (S_{sumfilm} - S_{fiber})/(S_{sumref} - S_{fiber}), \text{ where} \quad \text{(Eqn. 1)}$$

$R_{ref}$=reflectance of reference sample
$S_{film}$=signal from film sample
$S_{ref}$=signal from reference sample
$S_{sumfilm}$=total signal measured with film sample in place
$S_{fiber}$=reference signal from the fiber end (measured during baseline procedure)
$S_{sumref}$=total signal measured with reference sample in place Using Equation 1, and considering the conventional mode of operation of reflectance systems, the reference signal from the system component (e.g., fiber end) is treated as an always-present background signal, which is to be measured only so that its effects can be later negated by subtraction.

In contrast, embodiments of the reflectance system 100 treat the reference signal as a separate independent signal. In this manner, the reference signal of an embodiment provides a method to monitor, detect and/or compensate for drift in the host reflectance system. In an embodiment, the reference signal from the fiber end (or other component of the reflectance system 100) is measured immediately (e.g., approximately in a range of one millisecond to several seconds) before or after the reference signal is measured, but is not so limited. Later, either immediately before or after the sample signal is measured, the reference signal is again measured. Any changes detected between the first and second reference signal measurements are used to provide an indication of system drift. The system drift includes drift in one or more components of the reflectance system (e.g., light source, transmission element, spectrometer, etc.). To compensate for drift in the system, the following computation is made at each wavelength according to Equation 2:

$$R = R_{fibereff} * (S_{sumfilm} - S_{fiber})/S_{fiber}, \text{ where} \quad \text{(Eqn. 2)}$$

$R_{fibereff} = R_{ref} * (S_{fiber0})/(S_{sumref} - S_{fiber0})$
$R_{ref}$=reflectance of reference sample
$R_{fibereff}$=effective reflectance of the fiber end
$S_{fiber}$=reference signal from the fiber end immediately before or after measuring film sample
$S_{fiber0}$=reference signal from the fiber end immediately before or after measuring reference sample
$S_{sumfilm}$=total signal measured with film sample in place
$S_{sumref}$=total signal measured with reference sample in place Equation 2 reduces to Equation 1 when there is no change in the signal from the fiber end, that is, when there is no change in the reference signal taken at different points in time (e.g., when $S_{fiber} = S_{fiber0}$).

The reference signal from the fiber end (or from one or more other components of the host reflectance system) is always present (as long as there is illumination present), and this is the only signal received or detected when no reference or film sample is under analysis by the reflectance system. Because the total signal received is lowest when only the reference signal is present (e.g., when there is no sample signal or reference sample signal present), and because the reference signal is stable and varies less than five percent (5%) over several hours in typical metrology instruments, the reflectance system of an embodiment is configured to automatically track and record the reference signal from the distal end of the fiber between sample measurements. It is similarly straightforward to identify the reference signals from the distal end of the fiber that occur closest in time to the reference sample and/or film sample measurements.

As described above, an intermediate-reference reflection or signal (reference signal), which is present whether a sample is being measured or not, can be monitored relative to film sample measurements so as to be practically simultaneous and, thus, the intermediate-reference reflection can be used in an embodiment to detect and compensate for system drift. While the reference signal described above is generated from interaction or reflection of the illumination signal with the distal end of the fiber transmission element, alternative embodiments use a reference signal resulting from interactions with a variety of other components of the reflectance system. Generally, these other components can include one or more of a fiber, lens, mirror, and transparent sheet to name a few.

Figure 4:
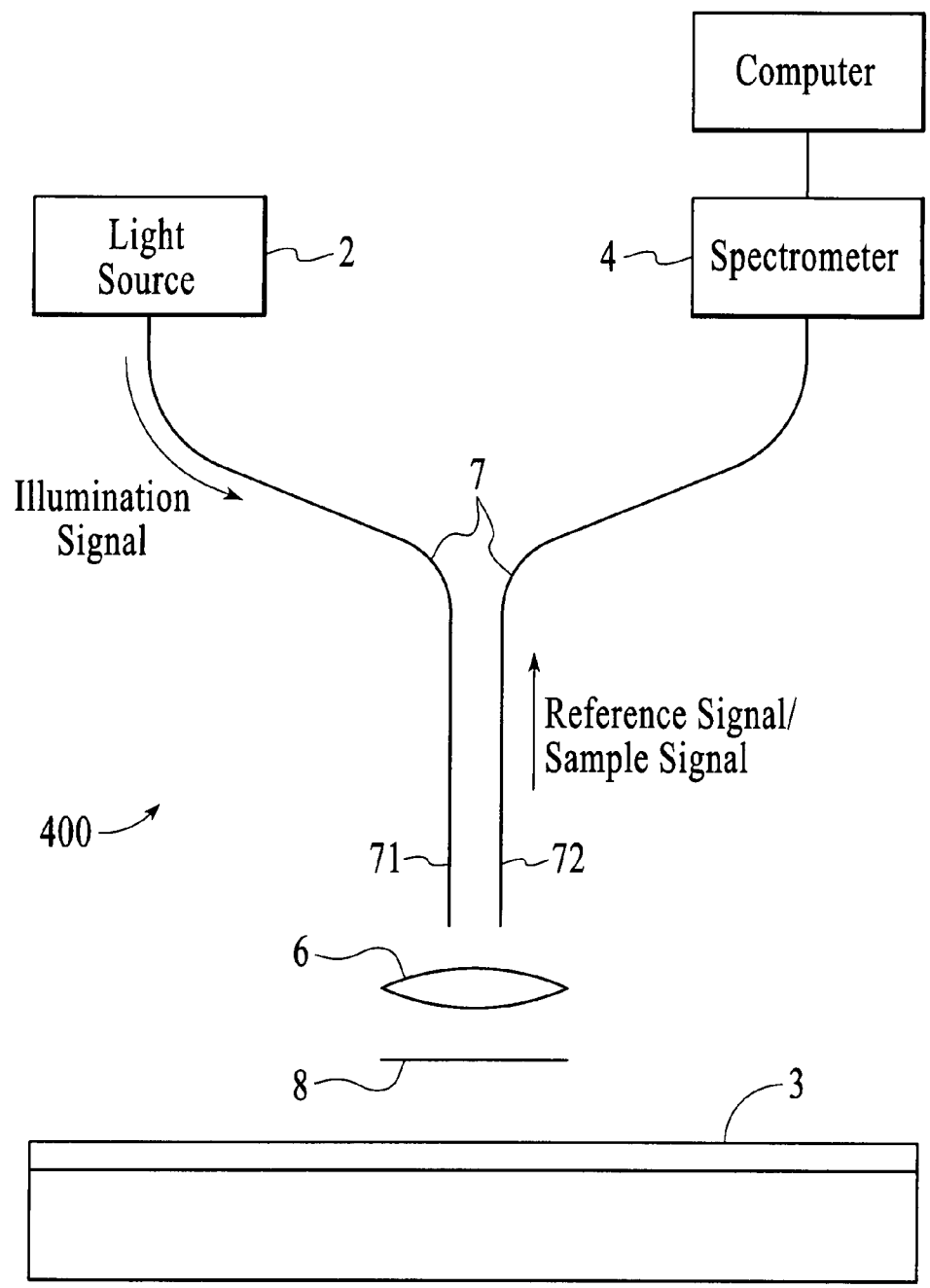
FIG. 4 is a reflectance system configured to include a reference signal, under an alternative embodiment.

FIG. 4 is a reflectance system 400 configured to include a reference signal, under an alternative embodiment. The system 400 includes a transmission element comprising a bifurcated fiber bundle 7. The bifurcated fiber bundle 7 includes an illumination fiber 71 coupled to a source of the illumination signal. The illumination fiber 71, also referred to herein as the first optical fiber 71, is configured to direct light from the source to a sample under analysis in the sample area. The bifurcated fiber bundle 7 also comprises a return fiber 72 coupled to the receiver. The return fiber 72, also referred to herein as the second optical fiber 72, is configured to direct signals (e.g., reference signal, sample signal, etc.) to the receiver. The return fiber 72 of this embodiment is coupled between the sample area and the spectrometer but is not so limited. The system 400 can include one or more lenses or mirrors 6 (optional) configured to relay light between the sample 3 (when present) and the bifurcated fiber bundle 7.

The system 400 also includes a transparent sheet 8 disposed near the sample area between distal ends of the illumination 71 and return 72 fibers and the sample (when present). The transparent sheet 8 is at least partially transparent in that it passes at least a portion of the illumination signal from the source toward a sample (when present) and passes at least a portion of the sample signal reflected from the sample (when present). Because the illumination fiber 71 and return fiber 72 are separate in this case, there is no reference signal reflected back into the return fiber 72 by any fiber end. Therefore, in this embodiment the intermediate reflection (reference signal) is provided by the transparent sheet 8. The transparent sheet 8, thus, generates the reference signal by virtue of interaction between the illumination signal and the transparent sheet 8.

Figure 5:
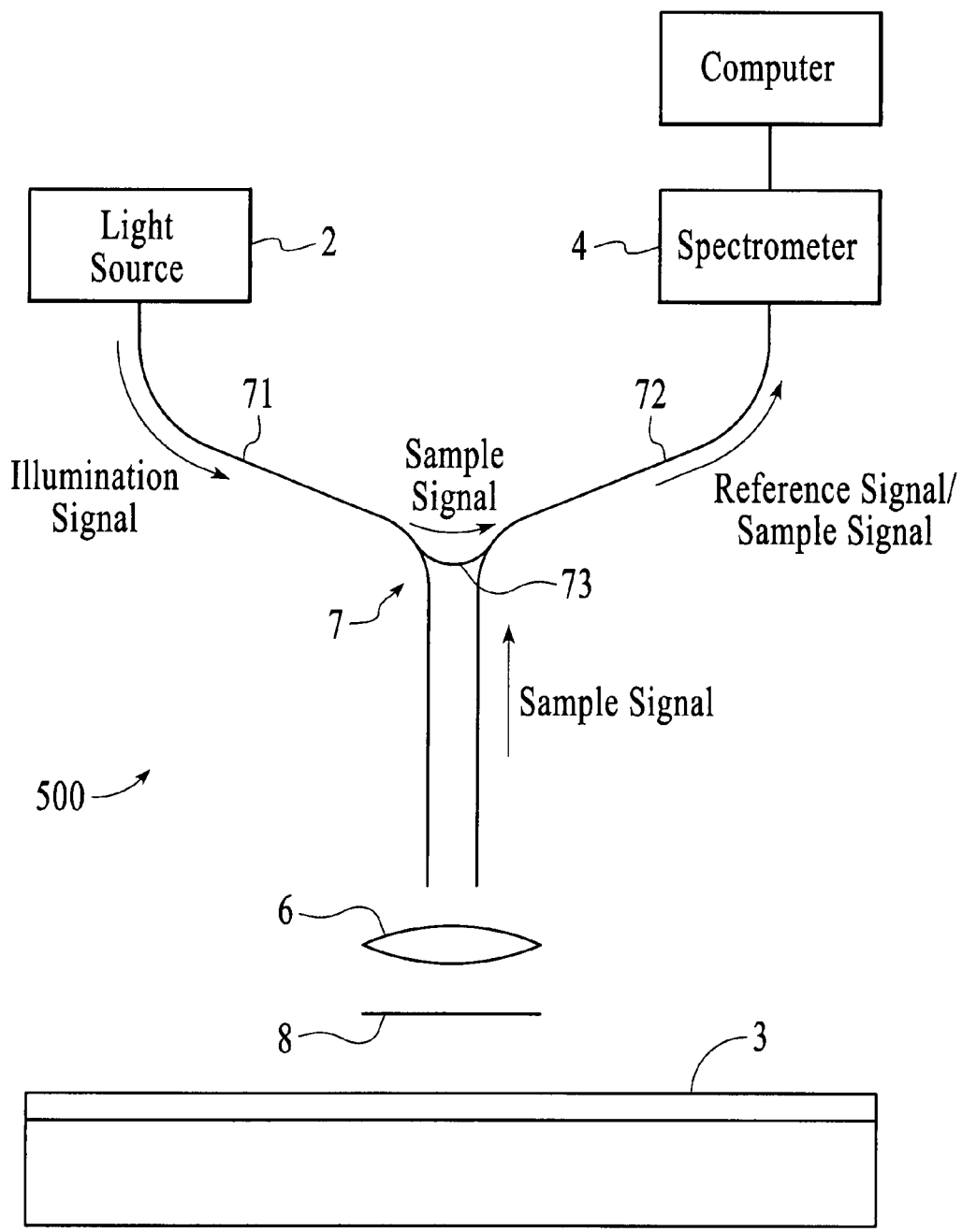
FIG. 5 is a reflectance system configured to include a reference signal, under another alternative embodiment.

FIG. 5 is a reflectance system 500 configured to include a reference signal, under another alternative embodiment. The system 500 includes a transmission element comprising a bifurcated fiber bundle 7. The bifurcated fiber bundle 7 includes an illumination fiber 71 coupled to a source of the illumination signal. The illumination fiber 71, also referred to herein as the first optical fiber 71, is configured to direct light from the source to a sample under analysis in the sample area. The bifurcated fiber bundle 7 also comprises a return fiber 72 coupled to the receiver. The return fiber 72, also referred to herein as the second optical fiber 72, is configured to direct signals (e.g., reference signal, sample signal, etc.) to the receiver. The return fiber 72 of this embodiment is coupled between the sample area and the spectrometer but is not so limited.

The bifurcated fiber bundle 7 also comprises a bridge fiber 73 coupled between the illumination 71 and return 72 fibers. The bridge fiber 73, also referred to herein as the third optical fiber 73, is configured to direct a signal to be used as a reference signal between the illumination 71 and return 72 fibers.

The system 500 can include one or more lenses or mirrors 6 (optional) configured to relay light between the sample (when present) and the bifurcated fiber bundle 7. The system 500 can also include a transparent sheet 8 disposed near the sample area between distal ends of the first and second optical fibers and the sample (when present). Because the illumination fiber 71 and return fiber 72 are separate in this case, there is no reference signal reflected back into the return fiber by a fiber end. However, in this embodiment the reference signal is provided by the bridge fiber 73, which functions to provide the reference signal by directly transferring a portion of the illumination signal from the illumination fiber 71 to the return fiber 72.

Figure 6:
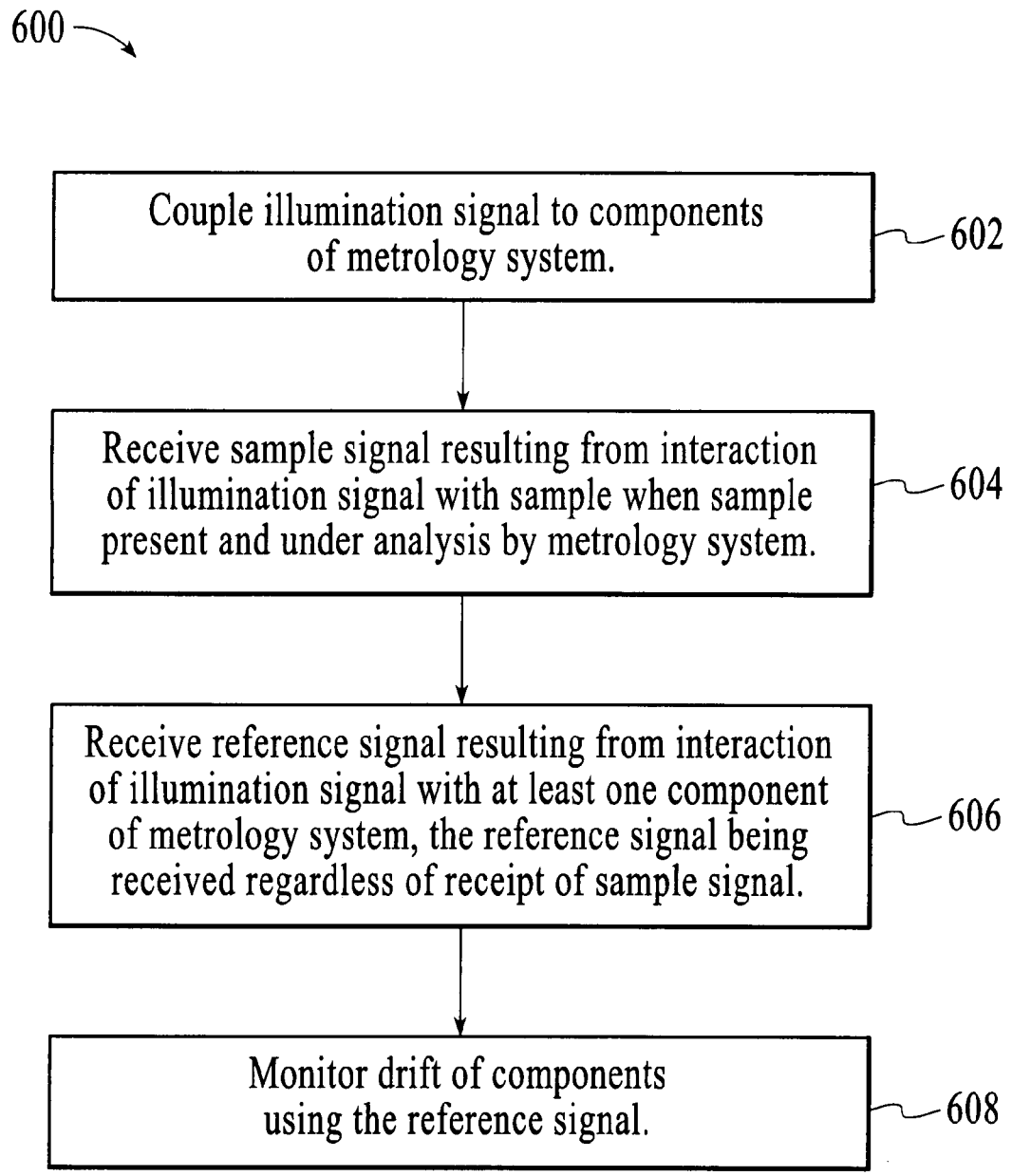
FIG. 6 is a flow diagram of a metrology method, under an embodiment.

FIG. 6 is a flow diagram of a metrology method 600, under an embodiment. The metrology method includes coupling 602 an illumination signal to components of a metrology system. The metrology method includes receiving 604 a sample signal that results from interaction of the illumination signal with a sample when the sample is present in the metrology system and under analysis. The metrology method further includes receiving 606 a reference signal that results from interaction of the illumination signal with at least one component of the metrology system components. The reference signal is present in the metrology system and received regardless of receipt of the sample signal. The method includes monitoring 608 drift of the components using the reference signal.

Aspects of the reflectance systems and methods described herein may be implemented as functionality programmed into any of a variety of circuitry. Some other possibilities for implementing aspects of the reflectance systems and methods include: microcontrollers with memory (such as electronically erasable programmable read-only memory (EEPROM)), embedded microprocessors, firmware, software, etc. Furthermore, aspects of the reflectance systems and methods may be embodied in microprocessors having software-based circuit emulation, discrete logic (sequential and combinatorial), custom devices, fuzzy (neural) logic, quantum devices, and hybrids of any of the above device types.

It should be noted that components of the various reflectance systems and methods disclosed herein may be described using computer aided design tools and expressed (or represented), as data and/or instructions embodied in various computer-readable media, in terms of their behavioral, register transfer, logic component, transistor, layout geometries, and/or other characteristics. Computer-readable media in which such formatted data and/or instructions may be embodied include, but are not limited to, non-volatile storage media in various forms (e.g., optical, magnetic or semiconductor storage media) and carrier waves that may be used to transfer such formatted data and/or instructions through wireless, optical, or wired signaling media or any combination thereof.

Examples of transfers of such formatted data and/or instructions by carrier waves include, but are not limited to, transfers (uploads, downloads, e-mail, etc.) over the Internet and/or other computer networks via one or more data transfer protocols (e.g., HTTP, FTP, SMTP, etc.). When received within a computer system via one or more computer-readable media, such data and/or instruction-based expressions of the above described systems and methods may be processed by a processing entity (e.g., one or more processors) within the computer system in conjunction with execution of one or more other computer programs.

Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

The above description of embodiments of the reflectance systems and methods is not intended to be exhaustive or to limit the systems and methods described to the precise form disclosed. While specific embodiments of, and examples for, the reflectance systems and methods are described herein for illustrative purposes, various equivalent modifications are possible within the scope of other reflectance systems and methods, as those skilled in the relevant art will recognize. The teachings of the reflectance systems and methods provided herein can be applied to other processing and measurement systems and methods, not only for the systems and methods described above.

The elements and acts of the various embodiments described above can be combined to provide further embodiments. These and other changes can be made to the reflectance systems and methods in light of the above detailed description.

In general, in the following claims, the terms used should not be construed to limit the reflectance systems and methods to the specific embodiments disclosed in the specification and the claims, but should be construed to include all systems and methods that operate under the claims. Accordingly, the reflectance systems and methods are not limited by the disclosure, but instead the scope of the reflectance systems and methods is to be determined entirely by the claims.

While certain aspects of the reflectance systems and methods are presented below in certain claim forms, the inventors contemplate the various aspects of the reflectance systems and methods in any number of claim forms. Accordingly, the inventors reserve the right to add additional claims after filing the application to pursue such additional claim forms for other aspects of the reflectance systems and methods.

What is claimed is:

1. A metrology method comprising:
   coupling an illumination signal to components of a metrology system;
   receiving a sample signal that results from interaction of the illumination signal with a sample when the sample is under analysis by the metrology system;
   receiving a reference signal that results from interaction of the illumination signal with at least one component of the components, wherein the reference signal is received regardless of receipt of the sample signal, wherein receiving the reference signal comprises one or more of measuring the reference signal prior to receiving the sample signal and measuring the reference signal subsequent to receiving the sample signal; and
   monitoring drift of the components using the reference signal.

2. The method of claim 1, wherein the illumination signal is a light signal.

3. The method of claim 1, wherein receiving the reference signal comprises receiving a first reflected signal, the first reflected signal generated during reflection of the illumination signal from a portion of the at least one component.

4. The method of claim 1, wherein receiving the reference signal comprises receiving at a second component a portion of the illumination signal from a first component.

5. The method of claim 1, wherein receiving the sample signal comprises receiving a second reflected signal from a surface of the sample, the second reflected signal generated during reflection of the illumination signal from the surface.

6. The method of claim 5, wherein the surface includes a film layer, wherein the second reflected signal includes light reflected from the film layer.

7. The method of claim 1, wherein the at least one component is a permanent non-moveable component of the metrology system.

8. The method of claim 1, wherein the at least one component is a light transmission element.

9. The method of claim 8, wherein the at least one component is one or more of an optical fiber, a lens, and a mirror.

10. The method of claim 1, wherein the at least one component is a distal end of an optical fiber through which the illumination signal is directed at the sample.

11. The method of claim 1, wherein the at least one component is a transparent sheet through which the illumination signal is directed at the sample.

12. The method of claim 1, comprising compensating for drift of the components using the reference signal.

13. The method of claim 12, comprising determining a correction factor for use in the compensating.

14. The method of claim 13, wherein determining the correction factor includes dividing a first value of the reference signal measured at a first time by a second value of the reference signal measured at a second time.

15. A reflectance system comprising components, wherein the components include a transmission element coupled to a sample area and a receiver, wherein the transmission element is configured to route signals between the components, wherein the signals include an illumination signal, a sample signal resulting from interaction of the illumination signal with a sample when the sample is in the sample area, and a reference signal resulting from interaction of the illumination signal with the components, wherein the reference signal is present regardless of presence of the sample signal and is used to monitor drift of the components, wherein the reference signal is one or more of measured prior to receipt of the sample signal and measured subsequent to receipt of the sample signal.

16. The system of claim 15, wherein the reference signal results from interaction of the illumination signal with the components including one or more of the transmission element, an optical fiber, a lens, and a mirror.

17. The system of claim 15, wherein the transmission element includes at least one optical fiber.

18. The system of claim 17, wherein the at least one optical fiber is an optical fiber in a Y-shaped configuration, wherein a first proximal end of the optical fiber is coupled to a source of the illumination signal, a second proximal end of the optical fiber is coupled to the receiver, and a distal end of the optical fiber directs light from the source at the sample area.

19. The system of claim 18, wherein the reference signal results from interaction of the illumination signal with the distal end of the optical fiber.

20. The system of claim 17, wherein the at least one optical fiber includes:
- a first optical fiber coupled to a source of the illumination signal, the first optical fiber configured to direct light from the source to the sample area; and
- a second optical fiber coupled to the receiver, the second optical fiber configured to direct the signals to the receiver.

21. The system of claim 20, comprising a transparent sheet disposed near the sample area and configured to be at least partially transparent to the illumination signal from the source and the sample signal from the sample.

22. The system of claim 21, wherein the reference signal results from interaction of the illumination signal with the transparent sheet.

23. The system of claim 20, comprising a third optical fiber coupled between the first optical fiber and the second optical fiber, wherein the third optical fiber transfers a portion of the illumination signal from the first to the second optical fiber, the portion of the illumination signal producing the reference signal.

24. The system of claim 15, wherein interaction of the illumination signal with the sample includes reflection of the illumination signal from a surface of the sample.

25. The system of claim 15, wherein the reference signal is used to compensate for drift of the components.

26. A computer readable medium including executable instructions which, when executed in a processing system, monitor drift in a metrology system by:
- coupling an illumination signal to components of the metrology system;
- receiving a sample signal that results from interaction of the illumination signal with a sample when the sample is under analysis by the metrology system;
- receiving a reference signal that results from interaction of the illumination signal with at least one component of the components, wherein the reference signal is received regardless of receipt of the sample signal, wherein receiving the reference signal comprises one or more of measuring the reference signal prior to receiving the sample signal and measuring the reference signal subsequent to receiving the sample signal; and
- monitoring drift of the components using the reference signal.

* * * * *